Figure 1:
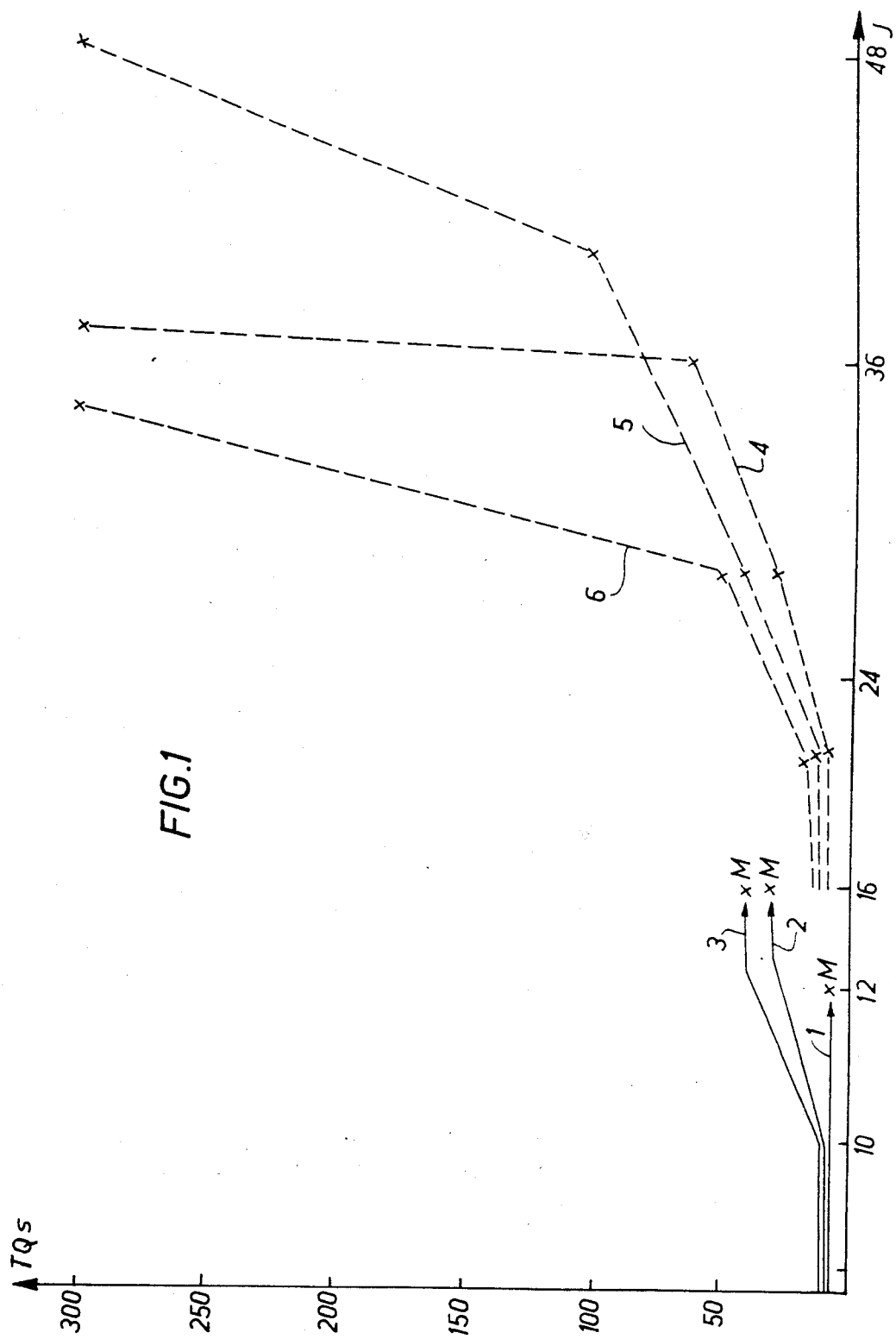
Figure 2:
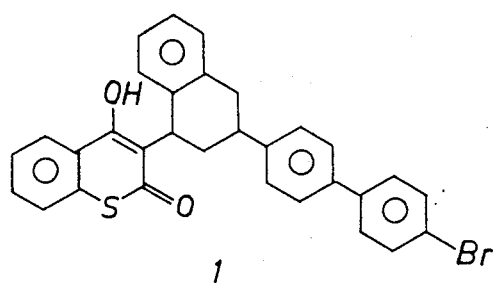
Figure 2:
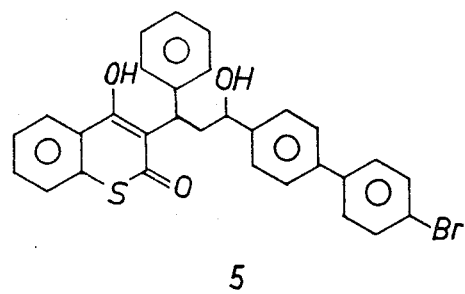
Figure 2:
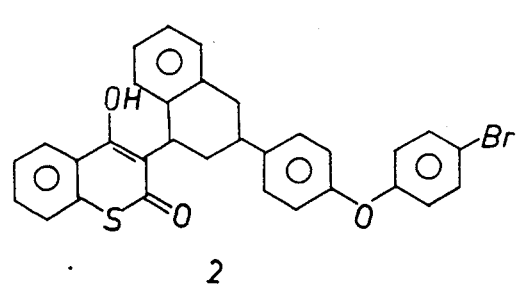
Figure 2:
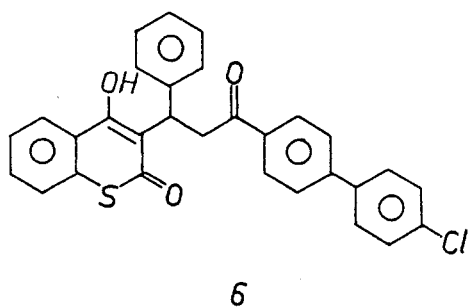
Figure 2:
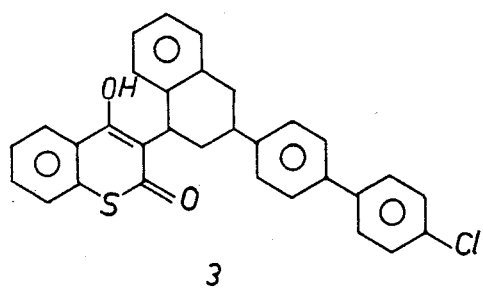
Figure 2:
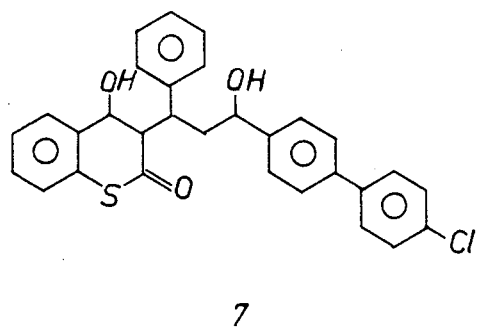
Figure 2:
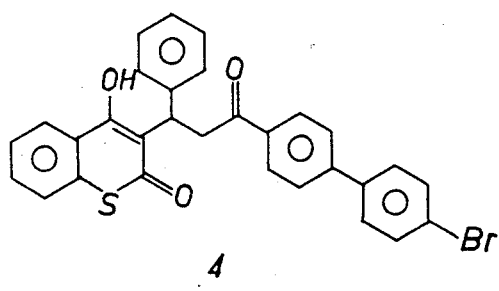
Figure 2:
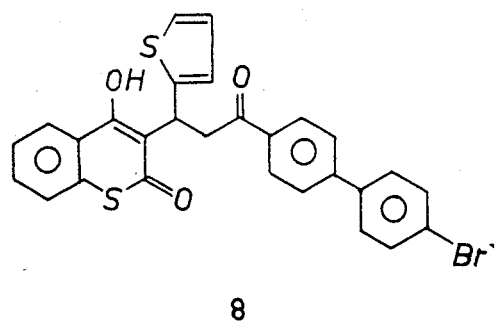

United States Patent [19]

Berthelon

[11] Patent Number: 4,585,786
[45] Date of Patent: Apr. 29, 1986

[54] RODENTICIDAL 4-HYDROXY-2H-1-BENZOTHIOPYRAN-2-ONE DERIVATIVES, COMPOSITIONS, AND METHOD OF USE THEREFOR

[75] Inventor: Jean-Jacques Berthelon, Decines-Charpieu, France

[73] Assignee: Lipha, Lyonnaise Industrielle Pharmaceutique, Lyons, France

[21] Appl. No.: 716,394

[22] Filed: Mar. 27, 1985

[30] Foreign Application Priority Data

Apr. 12, 1984 [FR] France ................. 84 05794

[51] Int. Cl.[4] ............... A61K 31/38; C07D 335/06
[52] U.S. Cl. ......................... 514/432; 549/23
[58] Field of Search ............. 549/23, 28, 285, 286; 514/432

[56] References Cited

U.S. PATENT DOCUMENTS 3,022,317  2/1982  Ziegler et al. .................. 549/23
3,764,693  10/1973  Boschetti et al. ................ 549/286
4,520,007  5/1985  Entwistle et al. ................ 549/285

FOREIGN PATENT DOCUMENTS 0547244  10/1950  Canada .................. 549/286

*Primary Examiner*—Henry R. Jiles
*Assistant Examiner*—J. G. Mullins
*Attorney, Agent, or Firm*—Browdy and Neimark

[57] ABSTRACT

The invention relates to hydroxy-4-2H-1-benzothiopyran-2-ones, represented by the following formula:

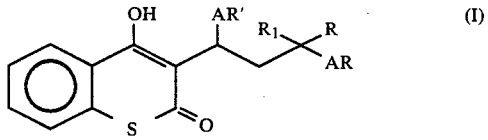

in which, when $R_1$ is hydrogen, R and AR' can form a tetrahydronaphtyl cycle; R and $R_1$ can form a carbonyl group; R is a hydroxyl group when $R_1$ is hydrogen; AR is a biphenyl or phenoxyphenyl group, which is substituted or non-substituted by a halogen, and AR' is a substituted or non-substituted phenyl group which may form with R a tetrahydronaphtyl cycle or a thienyl group. These compounds have interesting properties and may be used in particular as rodenticides.

12 Claims, 2 Drawing Figures

1

5

2

6

3

7

4

8

RODENTICIDAL 4-HYDROXY-2H-1-BENZOTHIOPYRAN-2-ONE DERIVATIVES, COMPOSITIONS, AND METHOD OF USE THEREFOR

The present invention relates to hydroxy-4-2H-1-benzothiopyran-2-ones of formula (I), their preparation and the compositions containing them.

These compounds are represented by the formula:

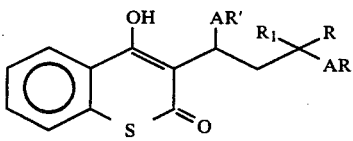

in which: R can form with AR' a tetrahydronaphtyl cycle when $R_1$ is hydrogen; R an $R_1$ may be a carbonyl group; R may be a hydroxyl group when $R_1$ is hydrogen; AR is a biphenyl or phenoxyphenyl group, which is substituted or non-substituted by a halogen; and AR' is a substituted or non-substituted phenyl group which may form with R a tetrahydronaphtyl cycle or a thienyl group.

These compounds may be prepared by one or the other of the following methods.

When in the formula (I) $RR_1=0$, the products are obtained by reacting hydroxy-4-2H-1-benzothiopyran-2-one with compounds of the following formula:

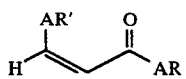

in a solvent such as ethanol or dioxane, in the presence of a condensation agent such as piperidine, at the boiling point for several hours.

When in the formula (I) R=H and $R_1$=OH, the compounds are obtained by reducing, by means of sodium borohydride in a solvent such as methanol, dimethylformamide or the mixture of one of these solvents with water, the compound of formula (I) in which $RR_1=0$.

In the case where R and AR' form a tetrahydronaphtyl cycle and $R_1$ is hydrogen, the compounds satisfying the formula (I) are prepared by reacting hydroxy-4-2H-1-benzothiopyran-2-one with a compound of the following formula:

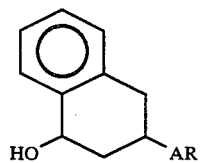

in a solvent, such as acetic acid, in the presence of sulfuric acid and between 20° C. and 150° C.

When $R_1$=OH or when R and R' form a tetrahydronaphtyl cycle and $R_1$ is hydrogen, the compounds are in the form of a mixture of diastereoisomers, as is shown in thin-layer chromatography or in high-pressure liquid chromatography.

The products of the invention have interesting properties in particulas as anti-coagulants, as shown by the results of tests carried out on the wild rat (Rattus Norvegious).

For this purpose, a bait with a dose of 50 ppm of the substance to be examined is prepared by impregnating wheat smeared with vaseline with a mixture consisting of starch and the compound under study. This bait is then given to adult male or female wild rats for 3 days and the activity is examined by ascertaining the mortality. The results obtained are shown in the following table I.

TABLE I

| Activity on *Rattus Norvegious* (breed sensitive to Coumafene) | | | |
|---|---|---|---|
| Compound | Dose | Duration of Treatment | Mortality |
| 1 | 50 ppm | 3 days | 10/10 |
| 2 | 50 ppm | 3 days | 10/10 |
| 3 | 50 ppm | 3 days | 10/10 |
| 4 | 50 ppm | 3 days | 10/10 |
| 5 | 50 ppm | 3 days | 10/10 |
| 6 | 50 ppm | 3 days | 10/10 |
| 7 | 50 ppm | 3 days | 10/10 |
| 8 | 50 ppm | 3 days | 10/10 |

(Coumafene=Warfarin=hydroxy-4-(phenyl-1-oxo-3 butyl)-3-2H-1 benzopyran-2-one).

The compounds have also shown that, in the case of a single dose, they result in a mortality of 100% on the Rattus Norvegious, as indicated in the following Table II:

TABLE II

| Activity on *Rattus Norvegious* (breed sensitive to Coumafene) | | | |
|---|---|---|---|
| Compound | Dose | Duration | Mortality |
| 1 | 50 ppm | 1 day | 10/10 |
| 2 | 50 ppm | 1 day | 10/10 |
| 3 | 50 ppm | 1 day | 10/10 |

Further, it has been found that the thiopyran derivatives (I) of the invention are superior to the corresponding pyran derivatives, which is a surprising result. Indeed, it is known that the derivatives of hydroxy-4 coumarin subtituted at position 3 are powerful anti-vitamin K agents and are used as rodenticides. The works of Mentzer, Bull. Soc. Chim. Biol. 25, pages 379-383 (1943) moreover showed that the replacement of heterocyclic oxygen of the dicoumarol by the sulfur resulted in a product of very little activity. The result was confirmed and, moreover, this was also ascertained in respect of the coumafene and its sulfur homologue thiocoumafene. The following Table III shows these results:

TABLE III

| Activity on *Rattus Norvegious* (breed sensitive to Coumafene) | | | |
|---|---|---|---|
| Compound | Dose | Duration | Mortality |
| Coumafene | 250 ppm | 3 days | 8/10 |
| thiocoumafene | 250 ppm | 3 days | 5/10 |

The preferred coumpound according to example 1, compared to its oxygenated equivalent (A) (bromo-4'-biphenyl-4)-3, tetrahydro-1,2,3,4-naphtyl-1)-3, hydroxy-4, 2H-1-benzopyran-2-one has an activity which is distinctly superior to the latter. The comparative tests were carried out on Rattus rattus (breed resisting Coumafene); Mus musculus (breed sensitive to Coumafene); Mus musculus (breed resisting Coumafene). The results obtained are shown in the following three tables:

TABLE IV

Test on *Rattus rattus* (breed resisting Coumafene)

| Compound | Dose | Duration of Administration | Mortality |
|---|---|---|---|
| 1 | 5 ppm | 2 days | 20/20 |
| A | 5 ppm | 2 days | 11/20 |

TABLE V

Test on *Mus musculus* (breed sensitive to Coumafene)

| Compound | Dose | Duration of Administration | Mortality |
|---|---|---|---|
| 1 | 5 ppm | 7 days | 20/20 |
| A | 5 ppm | 7 days | 15/20 |

TABLE VI

Test on *Mus musculus* (breed resisting Coumafene)

| Compound | Dose | Duration of Administration | Mortality |
|---|---|---|---|
| 1 | 5 ppm | 7 days | 10/10 |
| A | 5 ppm | 7 days | 7/10 |

These tables show that, in the case of compounds satisfying formula (I), the presence of the benzothiopyran cycle results in a superior activity relative to the analogous benzopyran.

Another unexpected effect obtained is the lower toxicity of the compound of the invention relative to their oxygenated homologues, in particular on the non-rodent species. By way of an example, the following test was carried out on a dog of the Beagle breed:

3 dogs of the beagle breed received 50 μg/kg of the compound according to Example 1, termed compound 1, daily by the oral route and 3 dogs of the Beagle breed received the same dose of the compound A according to the same protocol. The biological supervision included the determination of the Quick time with stoppage of the test when this reached 300 seconds. The curves in FIG. I of the accompanying drawing show the effects obtained on the lengthening of the Quick time in the Beagle dog, the Quick times in seconds are plotted as ordinates (TQs) and the durations of the treatment in days (j) are plotted as abscissae. The curves 1, 2 and 3 correspond to the effects of the compound A and the curves 4, 5 and 6 correspond to those of the compound 1. The letter M designates the moment of the death of an animal.

Further, it was noticed that in the case of dogs treated with the compound A, death occured very rapidly, as soon as the increase in the Quick time occured, which rendered the application of an antidote therapeutic impossible. On the other hand, in respect of the compound 1 of the invention, the increase in the Quick time and the deterioration of the clinical state are gradual. When the Quick time reaches 300 seconds, one has time to apply a conventional safeguarding treatment based on vitamin $K_1$: an I.V. injection of 5 mg/kg relayed by a treatment by the oral route. Thus, the 3 dogs revealed a rapid definitive return of the Quick time to normal values.

The compounds of the invention, and in particular the compound of Example 1, constitute anticoagulant active substances of rodenticide compositions in association with a support consumable by the rodents.

Examples are given here in after which illustrate the invention in a non-limiting manner.

EXAMPLE 1

[(Bromo-4'-biphenyl-4)3-tetrahydro-1,2,3,4-naphtyl-1]-3 hydroxy-4 2H-[1]-benzothiopyran-one-2. $C_{31}H_{23}BrO_2S$ (formula 1)

M.W.=539.47.

A solution of 14.2 g (0.08 mole) of hydroxy-4-2H-1-benzothiopyran-2-one and 30.2 g (0.08 mole) of (bromo-4'-biphenyl-4)-3-tetrahydro-1,2,3,4-naphtol-1 in 60 ml of acetic acid is brought to 110° C. 2.6 ml of concentrated sulfuric acid are then added and the heating is continued for 3 hours. After having cooled, the reaction medium is poured into water and the product is extracted with ether. The ether solution is washed with diluted soda and the insoluble oil formed is decanted and taken up with 10N hydrochloric acid. After extracting with ethyl acetate, evaporation and passage of the oil obtained on a silica column eluted with chloroform, the solid obtained is recrystalized in toluene. 9.5 g (rdt. 22%) of a white solid are obtained. $\gamma C=0$: 1600–1620 cm$^{-1}$.

| Analysis by weight: | C % | H % | Br % | S % | O % |
|---|---|---|---|---|---|
| Calculated | 69.01 | 4.30 | 14.81 | 5.94 | 5.93 |
| Found | 68.97 | 4.15 | 14.85 | 5.82 | |

An examination in thin-layer chromatography shows the presence in a variable proportion of two isomers, one being in the majority. There results in respect of the melting point a range which is in the case of the described product $MP_G=203°–227°$ C. By purification, it is possible to separate the two isomers, the majority isomer, when recrystalized in toluen, melts at 227°–230° C. The minority isomer melts at 209°–211° C.

EXAMPLE 2

[(Bromo-4' phenoxy)-4-phenyl)-3, tetrahydro-1,2,3,4-naphtyl-1]-3-hydroxy-4-2H-1-benzothiopyran-2-one. $C_{31}H_{23}BrO_3S$ (formula 2)

M.W.=555.47.

Prepared in accordance with Example 1 by using 6 g (0.015 mole) of [bromo-4' phenoxy-)-4-phenyl]-3, tetrahydro-1,2,3,4-naphtol-1 and 2.7 g (0.015 mole) of hydroxy-4-2H-1-benzothiopyran-2-one. After treating with hexane, a beige solid is obtained $MP_G$: 95°–105° C.
IR$\gamma C=0$: 1595.

| Analysis by weight: | C % | H % | Br % | O % | S % |
|---|---|---|---|---|---|
| Calculated | 67.03 | 4.17 | 14.39 | 8.64 | 5.77 |
| Found | 67.22 | 4.23 | 14.09 | | 5.79 |

EXAMPLE 3

[(Chloro-4'-biphenyl-4)-3-tetrahydro-1,2,3,4-naphtyl-1]-3, hydroxy-4-2H-[1]-benzothiopyran-one-2 (formula 3) $C_{31}H_{23}ClO_2S$

M.W.=495.01.

Prepared in accordance with Example 1 by using 7 g (0.04 mole) of hydroxy-4-2H-1-benzothiopyran-2-one and 13.4 g (0.04 mole) of (chloro-4'-biphenyl-4)-3, tetrahydro-1,2,3,4-naphtol-1. There is obtained, after purification in ethyl acetate, a whitish solid $MP_G$: 220°–2° C.
IR$\gamma C=0$: 1590.

| Analysis by weight: | C % | H % | Cl % | O % | S % |
|---|---|---|---|---|---|
| Calculated | 75.21 | 4.68 | 7.16 | 6.46 | 6.48 |
| Found | 75.19 | 4.72 | 7.02 | | 6.20 |

EXAMPLE 4

[(Bromo 4'-biphenyl-4)-3, oxo-3, phenyl-1] propyl-3-hydroxy-4-2H-[1]-benzothiopyran-one-2 (formula 4) $C_{30}H_{21}BrO_3S$

M.W.=541.45.

5 g (0.020 mole) of hydroxy-4-2H-1-benzothiopyran-one-2 and 9.1 g (0.025 mole) of (bromo-4' biphenyl-4)-3, phenyl-1-propenone-3 are placed in 50 ml of ethanol containing 0.4 ml of piperidine. This suspension is refluxed and the quantity of dioxane required to obtain a solution is added. The medium is then maintained by refluxing for 6 hours. After cooling to room temperature, the insoluble part is drain and the filtrate is highly cooled. The precipitate formed is drained and purified by passage on a silica column and then recrystallized in toluene. In this way a light beige solid is obtained.

MP$_G$: 160°-171° C.
IR$\gamma$C=O: 1580.

| Analysis by weight: | C % | H % | Br % | O % | S % |
|---|---|---|---|---|---|
| Calculated | 66.54 | 3.91 | 14.76 | 8.87 | 5.92 |
| Found | 66.43 | 3.82 | 14.73 | | 5.80 |

EXAMPLE 5

[(Bromo-4'-biphenyl-4)-3, hydroxy-3, phenyl-1] propyl-3, hydroxy-4-2H-[1]-benzothiopyran-one-2 (formula 5) $C_{30}H_{23}BrO_3S$

M.W.=543.46.

There are placed in a 250 ml reactor 7.9 g (0.0146 mole) of the product of Example 4, 70 ml of ethanol, 1.7 g (0.043 mole) of soda in the pellet form. The whole is then brought to 30° C. and 1.1 g (0.0292 mole) of sodium borohydride are added in small fractions. The product is then left for 2 hours at 30°-35° C., filtered and then the filtrate is poured on to the concentrated mixture H$_2$O—HCl (600 ml–30 ml). The white precipitate formed is drained and purified by passage on a silica column eluted with the cyclohexane-CHCl$_3$—MeOH mixture: 125—75—25.

MP$_G$: 110°-120° C.
IR$\gamma$C=O: 1600.

| Analysis by weight: | C % | H % | Br % | O % | S % |
|---|---|---|---|---|---|
| Calculated | 66.30 | 4.27 | 14.71 | 8.83 | 5.90 |
| Found | 66.25 | 4.28 | 14.82 | | 5.86 |

EXAMPLE 6

[(Chloro-4'-biphenyl-4)-3, oxo-3, phenyl-1] propyl-3 hydroxy-4-2H-[1]-benzothiopyran-one-2 (formula 6) $C_{30}H_{21}ClO_3S$

M.W.=496,99.

Prepared in accordance with Example 4 with 8.7 g (0.0273 mole) of (chloro-4' biphenyl-4)-3, phenyl-1-propenone-3 and 5.3 g (0.03 mole) of hydroxy-4-2H-[1]-benzothiopyran-one-2. After purification in toluene, a white solid is obtained.

MP$_G$: 171°-3° C.
IR$\gamma$C=O: 1590.

| Analysis by weight: | C % | H % | Cl % | O % | S % |
|---|---|---|---|---|---|
| Calculated | 72.50 | 4.26 | 7.13 | 9.66 | 6.45 |
| Found | 72.76 | 4.37 | 7.25 | | 6.21 |

EXAMPLE 7

[(Chloro-4'-biphenyl-4)-3, hydroxy-3, phenyl-1]-propyl-3, hydroxy-4-2H-[1]-benzothiopyran-one-2 (formula 7) $C_{30}H_{23}ClO_3S$

M.W.=499.

Prepared in accordance with Example 5 with 8 g (0.0161 mole) of the product of Example 6, 1.9 g (0.0474 mole) of soda in pellet form, 50 ml of dimethylformamide, 10 ml of water and 1.2 g (0.0322 mole) of sodium borohydride. A beige product is isolated.

MP$_G$: 105°-125° C. (decomposition).
IR$\gamma$C=O: 1585.

| Analysis by weight: | C % | H % | Cl % | S % | O % |
|---|---|---|---|---|---|
| Calculated | 72.20 | 4.65 | 7.11 | 6.42 | 9.62 |
| Found | 72.24 | 5.01 | 7.17 | 6.21 | |

EXAMPLE 8

[(Bromo-4'-biphenyl-4)-3, oxo-3, (thienyl-2)-1] propyl-3, hydroxy-4-2H-[1]-benzothiopyran-one-2 (formula 8) $C_{28}H_{19}BrO_3S_2$

M.W.=547,47.

Prepared in accordance with Example 4 with 11 g (0.03 mole) of (bromo-4-biphenyl-4)3-thienyl-2)-1-propenone-3 and 5.8 g (0.033 mole) of hydroxy-4-2H-[1]-benzothiopyran-one-2. By recrystallization in acetic acid, a white solid is obtained, MP$_G$: 140°-5° C.

IR$\gamma$C=O: 1600.

| Analysis by weight: | C % | H % | Br % | S % | O % |
|---|---|---|---|---|---|
| Calculated | 61.42 | 3.50 | 14.60 | 11.71 | 8.77 |
| Found | 61.65 | 3.52 | | 12.00 | |

I claim:

1. Hydroxy-4-2H-1-benzothiopyran-2-ones having the following formula:

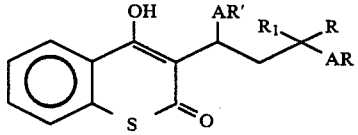

in which when R$_1$ is hydrogen, R and AR' may form a tetrahydronaphth-1H-yl radical; R and R$_1$ may form a carbonyl group; when R is hydrogen, R$_1$ may be a hydroxyl group; AR is a biphenyl or phenoxyphenyl group or biphenyl substituted by a halogen or phenoxyphenyl substituted by a halogen, AR' is a phenyl group or a thienyl group or may form with R a tetrahydronaphth-1H-yl when R$_1$ is hydrogen.

2. [(Bromo-4'-biphenyl-4)-3 tetrahydro-1,2,3,4-naphtyl-1]-3 hydroxy-4 2H-[1]-benzothiopyran-one-2, according to claim 1.

3. Hydroxy-4-2H-1-benzothiopyran-2-ones having the following formula:

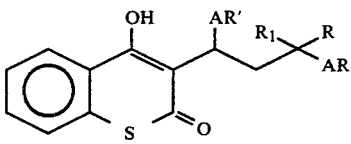

in which $R_1$ is hydrogen; AR is phenoxyphenyl substituted by a halogen or biphenyl substituted by a halogen; and AR' and R together form a tetrahydronapth-1H-yl radical.

4. The compound of claim 3 wherein AR is a biphenyl radical substituted by a halogen.

5. A rodenticide composition containing a rodenticidially effective amount of a compound according to claim 1 in association with a carrier which is consumable by rodents.

6. A rodenticide composition according to claim 5, containing as active substance [(bromo-4'-biphenyl-4)-3 tetrahydro-1,2,3,4-naphtyl-1]-3 hydroxy-4-2H-[1]-benzothiopyran-one-2.

7. A rodenticide composition containing a rodentically effective amount of a compound according to claim 3 in association with a carrier which is consumable by rodents.

8. A rodenticide composition containing a rodenticially effective amount of a compound according to claim 4.

9. A method of killing rodents comprising administering a rodenticicially effective amount of a hydroxy-4-2H-1-benzothiopyran-2-one having the following formula:

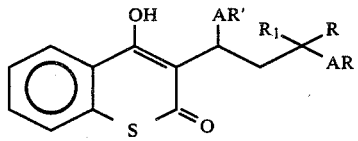

in which when $R_1$ is hydrogen, R and AR' may form a tetrahydronaphth-1H-yl radical; R and $R_1$ may form a carbonyl group; when R is a hydrogen, $R_1$ may be a hydroxyl group; AR is a biphenyl or phenoxyphenyl group or phenoxyphenyl substituted by a halogen or biphenyl substituted by a halogen, AR' is a phenyl group or a thienyl group or may form with R a tetrahydronaphth-1H-yl radical when $R_1$ is hydrogen, to a rodent.

10. The method of claim 9 wherein $R_1$ is hydrogen; R and AR' form a tetrahydronaphth-1H-yl radical; and AR is biphenyl and substituted by a halogen or phenoxyphenyl substituted by a halogen.

11. The method of claim 10 wherein AR is a biphenyl group substituted by a halogen.

12. The method of claim 11 wherein said halogen is bromine.

* * * * *